United States Patent
Kricheldorf et al.

(10) Patent No.: US 6,291,629 B1
(45) Date of Patent: Sep. 18, 2001

(54) CHIRALLY NEMATIC POLYESTERS

(75) Inventors: Hans R. Kricheldorf; Thorsten Krawinkel, both of Hamburg; Andreas Gerken, Schessel; Peter Schuhmacher, Mannheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/355,347

(22) PCT Filed: Feb. 5, 1998

(86) PCT No.: PCT/EP98/00620

§ 371 Date: Aug. 6, 1999

§ 102(e) Date: Aug. 6, 1999

(87) PCT Pub. No.: WO98/34974

PCT Pub. Date: Aug. 13, 1998

(30) Foreign Application Priority Data

Feb. 6, 1997 (DE) .............................. 197 04 506

(51) Int. Cl.⁷ .................................................. C08G 63/00
(52) U.S. Cl. ............................................................ 528/176
(58) Field of Search ............................................. 528/176

(56) References Cited

U.S. PATENT DOCUMENTS

| | | |
|---|---|---|
| 5,362,315 | 11/1994 | Mueller-Rees et al. ............. 106/493 |
| 5,691,053 | 11/1997 | Gailberger et al. .................. 428/357 |
| 5,766,679 | 6/1998 | Siemensmeyer et al. ........ 427/207.1 |
| 5,798,147 | 8/1998 | Beck et al. ............................ 429/511 |
| 5,851,604 | 12/1998 | Mueller-Rees et al. .................. 428/1 |
| 5,876,837 | 3/1999 | Sailer et al. .......................... 428/195 |

FOREIGN PATENT DOCUMENTS

| | | |
|---|---|---|
| 2166755 | 5/1986 | (GB) . |
| WO 95/29961 | 11/1995 | (WO) . |
| WO 95/29962 | 11/1995 | (WO) . |
| WO 96/02597 | 2/1996 | (WO) . |

OTHER PUBLICATIONS

G.W. Gray, et al., eds., Liquid Crystals & Plastic Crystals, Table of Contents, 1974, (7 pages).

H. Baessler, Festkoerperprobleme XI, pp. 99–133, "Liquid Crystals", 1971.

H. Baessler, et al., The Journal of Chemical Physics, vol. 52, No. 2, pp. 631–637, "Helical Twisting Power of Steroidal Solutes in Cholesteric Mesophases", Jan. 15, 1970.

I. Heynderickx, et al., Mol. Cryst. Liq. Cryst., vol. 203, pp. 113–126, "The Use of Cholesterically–Ordered Polymer Networks in Practical Applications", 1991.

S. Vilasagar, et al., Mol. Cryst. Liq. Cryst., vol. 56 (Letters), pp. 263–269, "Cholesteric, Thermotropic Polymers with Mesogenic Moieties and Flexible Spacers in the Main Chain", 1980.

A. Blumstein, et al., Journal of Polymer Science: Polymer Physics Edition, vol. 20, pp. 877–892, "Nematic and Cholesteric Thermotropic Polyesters with Azoxybenzene Mesogenic Units and Flexible Spacers in the Main Chain", 1982.

E. Chiellini, et al., Polymer Bulletin, vol. 9, pp. 336–343, "Chiral Liquid Crystal Polymers 3. Structurally Ordered Thermotropic Polyesters of Optically Active Propyleneglycol Ethers", 1983.

V.V. Zuyev, et al., Vysokomol. Soedin., Ser. B, vol. 34, No. 3, pp. 47–54, 1992, (In Russian).

V.V. Zuyev, et al., Vysokomol. Soedin, Ser. B, vol. 31, No. 2, pp. 130–132, 1989, (In Russian).

Derwent Abstracts, AN 98–121307/12, DE 19631658, Feb. 12, 1998, (5 pages).

Derwent Abstracts, AN 96–343521/35, EP 724005, Jul. 31, 1996, (2 pages).

H.R. Kricheldorf, et al., Macromolecules, vol. 28, pp. 6565–6570, "Liquid–Crystalline Polyimides. 20. Photoreactive and Cholesteric Poly(ester–imide)s Based on 4–Aminocinnamic Acid Trimellitimide and Chiral Sulfide Spacers", 1995.

J. Stumpe, et al., Macromolecules, vol. 28, pp. 5306–5311, "Photoreactive Cholesteric Polyesters Derived From 4–Carboxycinnamic Acid and Novel Chiral Spacers", 1995.

H.R. Kricheldorf, et al., High Perform. Polym., vol. 7, pp. 471–480, "LC–Polyimides 26. Photoreactive, Nematic or Cholesteric Poly(ester–imide)s Derived From 4–Aminocinnamic Acid Trimellitimide, Isosorbide and Various Diphenols", 1995, (Missing pp. 476–477, will be filed later).

H.R. Kricheldorf, et al., Macromol. Rapid Commun., vol. 16, pp. 231–237, "Liquid–Crystalline Polyimides, 16ᵃ⁾ Chiral Thermotropic Copoly(ester–imide)s Based on Isosorbideᵇ⁾ and N–(4–Carboxyphenyl) Trimellitimide", 1995.

N. Probst, et al., High Perform. Polym., vol. 7, pp. 461–469, "LC–Polyimides 24. Cholesteric Copoly(ester–imide)s Derived from 4–Aminobenzoic Trimellitimide and Isomannide or 1,3–Butanediol", 1995.

H.J. Park, et al., Polymer, vol. 26 (Conference Issue), pp. 1301–1306, "Liquid Crystal Polymers: 19. Cholesteric Main Chain Polyesters with Triad Aromatic Ester Mesogenic Units and Chiral Polyalkylene Spacers", Aug., 1985.

J.I. Jin, et al., Polymer Journal, vol. 18, No. 1, pp. 99–101, "Miscibility of Main–Chain Thermotropic Polyesters", 1986.

J.I. Jin, et al., Polymer (Korea), vol. 10, No. 4, pp. 382–388, "Main Chain Cholesteric Copolyesters Containing Chiral 3–Methyladipoyl Moiety in the Spacers", Aug., 1986.

(List continued on next page.)

Primary Examiner—Terressa M. Boykin
(74) Attorney, Agent, or Firm—Oblon, Spivak, McClelland, Maier & Neustadt, P.C.

(57) ABSTRACT

Liquid crystalline chiral nematic polyesters have flexible chains comprising isosorbide, isomannide and/or isoidide units. The polyesters are not crystalline and form stable Grandjean textures which can be frozen on cooling below the glass transition temperature. They can therefore be used in particular as surface-coating materials.

23 Claims, No Drawings

OTHER PUBLICATIONS

J.I. Jin, et al., Polymer (Korea), vol. 10, No. 6, pp. 635–640, "Thermotropic Compounds Having Two Terminal Mesogenic Units and Central Spacers. 9. Miscibility Between Dimesogenic, Nematic Compounds and Nematic or Cholesteric Polyesters", Oct., 1986.

J.M.G. Cowie, et al., Makromol. Chem., vol. 189, pp. 1511–1516, "Thermotropic Liquid–Crystalline Main–Chain Polyesters Containing Cyclooctylene Units, $6^{a)}$", 1988.

V.V. Zuyev, et al., Polymer Science U.S.S.R., vol. 31, No. 5, pp. 1161–1167, "Synthesis of Liquid–Crystal Copolymers Containing Alicyclic Fragments in the Main Chain", 1989.

A.S. Angeloni, et al., Liquid Crystals, vol. 4, No. 5, pp. 513–527, "Photochromic Liquid–Crystalline Polymers Main Chain and Side Chain Polymers Containing Azobenzene Mesogens", 1989.

K. Fujishiro, et al., Macromolecules, vol. 25, pp. 88–95, "Main–Chain Cholesteric Liquid Crystalline Polyesters with Chiral Pendant Groups. 2. Cholesteric Copolyesters Containing Chiral and Achiral Substituted Hydroquinones", 1992.

K. Fujishiro, et al., Macromolecules, vol. 25, pp. 81–87, "Main–Chain Cholesteric Liquid Crystalline Polyesters with Chiral Pendant Groups. 1, Model Compounds and Polyesters Containing a Chiral Substituted Hydroquinone", 1992.

CHIRALLY NEMATIC POLYESTERS

The invention relates to liquid crystalline chiral nematic polyesters.

Liquid crystalline phases, called mesophases, may occur on heating substances with shape anisotropy. The individual phases differ by the spatial arrangement of the centers of mass of the molecules on the one hand and by the arrangement of the molecules with respect to the long axes on the other hand (G. W. Gray, P. A. Winsor, Liquid Crystals and Plastic Crystals, Ellis Horwood Limited, Chichester 1974). The nematic liquid crystalline phase is distinguished by parallel orientation of the long axes of the molecules (one-dimensional order state). Provided that the molecules forming the nematic phase are chiral, the result is a chiral nematic (cholesteric) phase in which the long axes of the molecules form a helical superstructure perpendicular thereto (H. Baessler, Festkörperprobleme XI, 1971). The chiral moiety may be present in the liquid crystalline molecule itself or else be added as dopant to the nematic phase, inducing the chiral nematic phase. This phenomenon was first investigated on cholesterol derivatives (eg. H. Baessler, M. M. Labes, *J. Chem. Phys.* 52 (1970) 631).

The chiral nematic phase has special optical properties: a high optical rotation and a pronounced circular dichroism resulting from selective reflection of circularly polarized light within the chiral nematic layer. If the pitch of the helical superstructure corresponds to the wavelength of visible light, there is formation of what is called a Grandjean texture. The colors appear different depending on the angle of view and depend on the pitch of the helical superstructure, which in turn depends on the twisting ability of the chiral component. It is possible in this case, in particular by altering the concentration of a chiral dopant, to vary the pitch and thus the wavelength range of the selectively reflected light of a chiral nematic layer. Chiral nematic systems of this type have interesting possibilities for practical use. Thus, a stable, colored network can be produced by incorporating chiral moieties into mesogenic acrylates and orienting in the chiral nematic phase, eg. after photocrosslinking, but the concentration of chiral component therein can no longer be changed (G. Galli, M. Laus, A. Angelon, *Makromol. Chemie* 187 (1986) 2289). Admixing noncrosslinkable chiral compounds to nematic acrylates makes it possible to prepare, by photocrosslinking, a colored polymer which still contains large amounts of soluble components (I. Heyndricks, D. *J. Broer, Mol. Cryst. Liq. Cryst.* 203 (1991) 113). It is furthermore possible, by random hydrosilylation of mixtures of cholesterol derivatives and acrylate-containing mesogens with defined cyclic siloxanes and subsequent photopolymerization, to obtain a chiral nematic network in which the chiral component may form a proportion of up to 50% of the material employed; however, these polymers still contain marked amounts of soluble materials (F. H. Kreuzer, R. Mauerer, Ch. Müller-Rees, J. Stohrer, Contribution No. 7, 22nd Liquid Crystals Meeting, Freiburg, 1993).

DE-A-35 35 547 describes a process in which a mixture of cholesterol-containing monoacrylates can be processed, by photocrosslinking, to chiral nematic layers. However, the total amount of the chiral component in the mixture is about 94%. Although a material of this type, as pure side chain polymer, does not have very high mechanical stability, the stability can be increased by highly crosslinking diluents.

Many chiral nematic polyesters in which the mesogenic structures are incorporated into the main chain are also known, eg. from S. Vilasagar, A. Blumstein, *Mol. Cryst. Liq. Cryst.* (1980), 56 (8), 263–9; A. Blumstein, S. Vilasagar, S. Ponratham, S. B. Clough, R. B. Blumstein, G. Maret, *J. Polym. Sci. , Polym. Phys. Ed.* (1982), 20 (5), 877–92; E. Chiellini, G. Galli, C. Malanga, N. Spassky, *Polym. Bull.* (1983), 9 (6–7), 336–43); H. J. Park, J. I. Jin, R. W. Leng, *Polymer* (1985), 26 (9), 1301–6; J. I. Jin, E. J. Choi, K. Y. Lee, *Polym. J.* (1986), 18 (1), 99.101; J. I. Jin, S. C. Lee, S. D. Chi, J. H. Chang; *Pollimo* (1986), 10 (4), 382–8; J. I. Jin, E. J. Choi, B. W. Jo, *Pollimo* (1986), 10 (6), 635–40; J. M. G. Cowie, H. H. Wu, *Makromol. Chem.* (1988), 189 (7), 1511–16; V. V. Zuev, I. G. Denisov, S. S. Skorokhodov, *Vysokomol. Soedin., Ser. A* (1989, 31 (5), 1056–61; A. S.

Angeloni, D. Caretti, C. Carlini, E. Chiellini, G. Galli, A. Altomare, R. Solaro, M. Laus, *Liq. Cryst.* (1986), 4 (5), 513–27; K. Fujishiro, R. W. Lenz, *Macromolecules* (1992), 25 (1), 88–95; K. Fujishiro, R. W. Lenz, *Macromolecules* (1992), 25 (1), 81–7; V. V. Zuev, I. G. Denisov, S. S. Skorokhodov, *Vysokomol. Soedin., Ser. B* (1992), 34 (3), 47–54); V. V. Zuev, I. G. Denisov, 40 S. S. *Skorokhodov Vysokomol. Soedin., Ser. B* (1989), 31 (2), 130–2.

These polyesters as a rule have narrow ranges of existence of the chiral nematic phase and contain mainly open-chain chiral components which have a low twisting ability so that relatively large contents of these components are necessary in order to obtain a color. This limits the choice of the remaining polyester constituents, eg. in respect of their mechanical properties.

DE-A-19504913.6 describes chiral nematic polyesters with strongly twisting chiral diol components, in particular dianhydro sugars, and wide liquid crystalline phase ranges.

EP-A-682 092 describes surface coatings based on chiral nematic polymers. Examples mentioned are polyesters prepared by polycondensation of dicarboxylic acids and diols.

DE-A-19631658 describes chiral nematic polycarbonates prepared by various types of polycondensation of diols with phosgene or diphosgene.

DE-A-44 41 651 discloses a process for the surface coating of substrates with a coating composition which contains at least one polymerizable low molecular weight liquid crystalline compound. The use of, in particular, photochemically polymerizable, low molecular weight liquid crystalline compounds (oligoesters) in printing inks, other inks and surface-coating systems, is also described.

WO-A-96 02 597 likewise describes a process for coating or printing substances with a coating or printing composition which contains a chiral or achiral liquid crystalline monomer and a non-liquid crystalline chiral compound. The liquid crystalline monomers are preferably photochemically polymerizable bisacrylates.

WO-A-95 29 962 describes aqueous coating compositions for producing coatings whose apparent color depends on the angle of inspection and which contain pigments in platelet form from oriented, three-dimensionally crosslinked substances with a liquid crystalline structure with a chiral phase. Substances described as particularly preferred are three-dimensionally crosslinkable polyorganosiloxanes.

WO-A-95 29 961 discloses coating compositions whose apparent color depends on the angle of inspection, and use thereof in basecoats for multilayer coatings. The compositions contain pigments in platelet form, which have a color depending on the angle of inspection and consist of oriented, three-dimensionally crosslinked substances with a liquid crystalline structure with a chiral phase. Substances described as preferred are three-dimensionally crosslinkable polyorganosiloxanes.

DE-A-44 18 076 describes an effect coating composition and an effect coating using liquid crystalline interference pigments. The interference pigments consist of esterified cellulose ethers, in particular acylated hydroxypropylcellulose.

EP-A-724 005 discloses a pigment with a color which depends on the angle of inspection, its preparation and use in a surface coating composition. The pigment is obtained by three-dimensional crosslinking of oriented substances with a liquid crystalline structure with a chiral phase. Preferred substances are three-dimensionally crosslinkable polyorganosiloxanes. In order to make the pigment retain its color at elevated temperatures, it is proposed to carry out the crosslinking in the presence of at least one other compound of neutral color which contains at least two crosslinkable double bonds. Preferred compounds of neutral color which are mentioned are acrylates, polyurethanes, epoxides, siloxanes, polyesters and alkyd resins.

EP-A-0686 674 and the priority application DE-A-44 16 191 on which it is based describe interference pigments consisting of molecules fixed in a cholesteric arrangement, and their use. The described pigments have a platelet-like structure and a thickness of from 1 $\mu$m to 20 $\mu$m. They contain oriented crosslinked substances with a liquid crystalline structure with a chiral phase (preferably polyorganosiloxanes).

EP-A-0601 483 and the priority application DE-A-42 40 743 on which it is based describe pigments with a color which depends on the angle of inspection, their preparation and use. The described pigments consist of oriented three-dimensionally crosslinked substances with a liquid crystalline structure with a chiral phase (preferably polyorganosiloxanes) with or without other dyes and pigments. The other dyes and pigments which may be present do not in this case act as carrier for the oriented three-dimensionally crosslinked liquid crystalline substances with a chiral phase.

One of the main problems in the provision of chiral nematic polyesters is the fixing of the Grandjean texture. Various methods for fixing Grandjean textures by crosslinking via a bonds have recently been published (H. R. Kricheldorf, N. Probst, M. Gurau, M. Berghahn, Macromolecules 28 (1995) 6565, J. Stumpe, A. Ziegler, M. Berghahn, H. R. Kricheldorf; Macromolecules 28 (1995) 5306; H. R. Kricheldorf, N. Probst; High Perform. Polym. 7 (1995) 471–480). These methods comprise photocrosslinking of UV-sensitive chiral nematic polymers. However, two disadvantages are common to all types of crosslinking. In the first place, the crosslinking process alters the chemical structure of the polymers, and thus also frequently the supermolecular arrangement on which formation of the Grandjean texture depends. In the second place, polymers to be crosslinked must undergo an additional, industrially elaborate curing step.

Another problem in the provision of chiral nematic polyesters is the fact that most liquid crystalline polymers described in the literature, and all commercially obtainable liquid crystalline polymers are semicrystalline materials. Semicrystalline materials are, however, unsuitable for many applications because the scattering of light by the crystallites greatly reduces the brightness and brilliance of the colors.

H. R. Kricheldorf, N. Probst; Macromol. Rapid. Commun. 16 (1995) 231 and N. Probst, H. R. Kricheldorf; High Perform. Polym. 7 (1995) 461 disclose chiral nematic copoly(ester-imides) which have little tendency to crystallize (<20%) but which form unstable Grandjean textures usually only above 300° C. These polymers contain isosorbide or isomannide as chiral diol component.

It has now been found, surprisingly, that polyesters which comprise isosorbide, isomannide or isoidide units, and alkylene-containing diol or dicarboxylic acid units which flexibilize the polyester chain, form stable Grandjean textures without displaying an increased tendency to crystallize. They can be fixed without crosslinking and without the disadvantages described above, and can be prepared straightforwardly and at low cost.

The present invention therefore relates to chiral nematic polyesters with flexible chains which comprise isosorbide, isomannide and/or isoidide units, preferably isosorbide units, and, for flexibilization of the chains, contain at least one unit selected from (and derived from)

(a) aliphatic dicarboxylic acids,
(b) aromatic dicarboxylic acids with a flexible spacer,
(c) $\alpha,\omega$-alkanediols,
(d) diphenols with a flexible spacer and
(e) condensates of a polyalkylene terephthalate or polyalkylene naphthalate with an acylated diphenol and an acylated isosorbide.

The polyesters according to the invention are non-crystalline and form stable Grandjean textures which can be frozen on cooling below the glass transition temperature. The glass transition temperatures of the polyesters in turn are, despite the flexibilization, above 80° C., preferably above 90° C., in particular above 100° C.

The polyesters according to the invention are preferably composed of dicarboxylic acids and diols.

The polyesters according to the invention comprise as units (a) preferably those of the formula

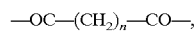

where n is a number in the range from 3 to 15, in particular 4 to 12, and particularly preferably adipic acid;
as units (b) preferably those of the formula

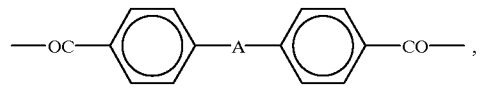

where
A is $(CH_2)_n$, $O(CH_2)_nO$ or $(CH_2)_o$—O—$(CH_2)_p$,
n is a number in the range from 3 to 15, in particular 4 to 12, particularly preferably 4 to 10, and
o and p are, independently of one another, a number in the range from 1 to 7;
as units (c) preferably those of the formula

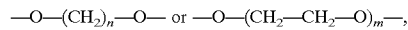

where
n is a number in the range from 3 to 15, in particular 4 to 12, particularly preferably 4 to 10, and
m is a number in the range from 1 to 10; and
as units (d) preferably those of the formula

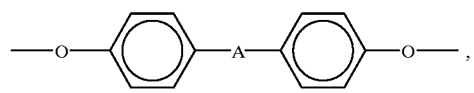

where
A is $(CH_2)_n$, $O(CH_2)_nO$ or $(CH_2)_o$—O—$(CH_2)_p$,
n is a number in the range from 3 to 15, in particular 4 to 12, particularly preferably 4 to 10, and o and p are, indepedently of one another, a number in the range from 1 to 7.

The polyesters according to the invention additionally comprise as nonflexible acid component preferably dicarboxylic acid units of the formula
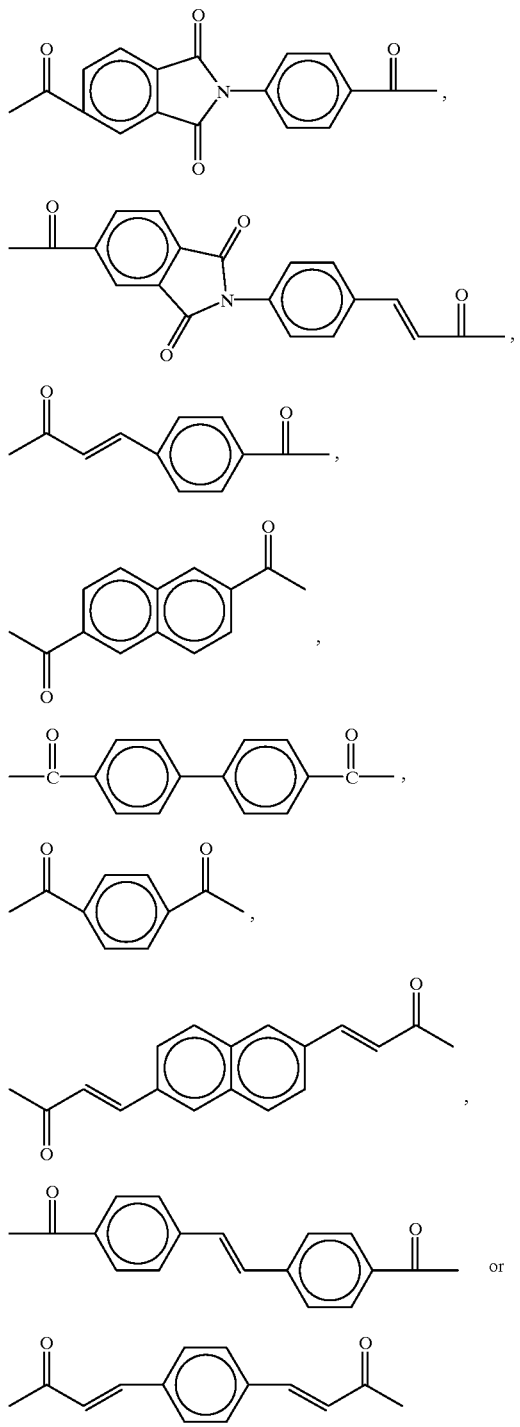
and as nonflexible alcohol component diol units of the formula
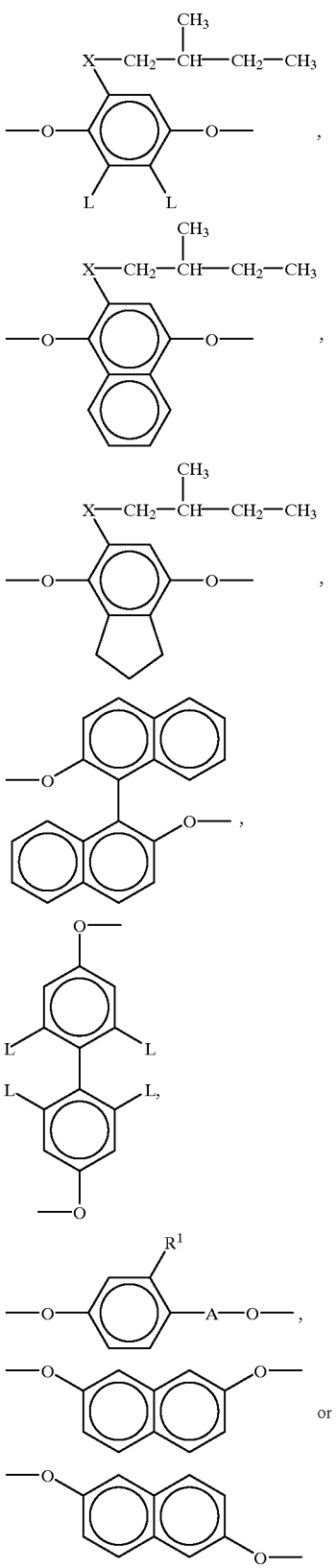

where in the above formulae

L is alkyl, alkoxy, halogen, COOR, OCOR, CONHR or NHCOR,

X is S, O, N, CH$_2$ or a single bond,

A is a single bond,

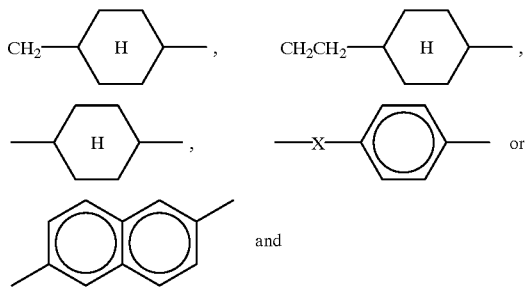

R$^1$ is hydrogen, halogen, alkyl or phenyl, and

R is alkyl or hydrogen.

The polyesters according to the invention may comprise additional flexible diol units of the formula

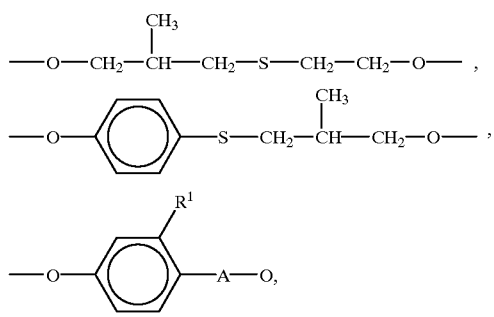

where

R$^1$ is hydrogen, halogen, alkyl or phenyl,

A is (CH$_2$)$_n$, O(CH$_2$)$_n$, S(CH$_2$)n or NR(CH$_2$)$_n$, and n is a number from 1 to 15.

The content of isosorbide, isomannide and/or isoidide units of the formulae:

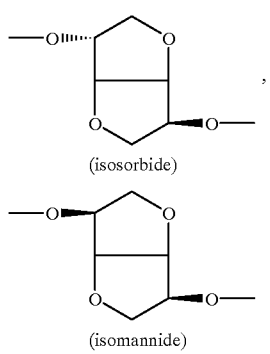
(isosorbide)

(isomannide)

and

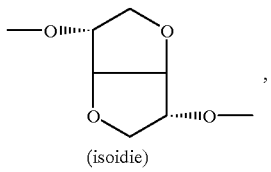
(isoidie)

is preferably in the range of about 1–15 mol %, in particular about 2.5–10 mol %, of the total content of structural units and in the range of about 2–30 mol %, in particular about 5–20 mol %, of the content of diol units. Said units are advantageously distinguished by a very high twisting ability and by great chemical and thermal stability.

The content of units flexibilizing the polyester chain is preferably about 1–50 mol %, in particular 5–30 mol %, of the total content of structural units.

The polyesters according to the invention can be prepared by various types of polycondensation or by transesterification of polyesters with a mixture of acid component and acylated alcohol component.

Examples of conventional types of polycondensation are the HCl process, the silyl process, and the transesterification process. These processes are disclosed inter alia by H. R. Kricheldorf, N. Probst; Macromol. Rapid. Commun. 16 (1995) 231 and N. Probst, H. R. Kricheldorf; High Perform. Polym. 7 (1995) 461.

The acid component and alcohol component are employed in the molar ratio of about 1:1.

The reaction time may vary within wide limits and is generally from 1 to 48 h, in particular 1 to 24 h.

The reaction is carried out at elevated temperature, generally in the range from 120° C. to 300° C., it also being possible to increase the temperature stepwise in this range.

In the HCl process, the free diols are dissolved with the dichlorides of the dicarboxylic acids in a suitable organic solvent, eg. an ether such as dioxane, a chlorinated hydrocarbon such as 1,1,2,2-tetrachloroethane, 1-chloronaphthalene or 1,2-dichlorobenzene, in a suitable reaction vessel. An example of a suitable reaction vessel is a pressure-tight stirred container with gas inlet and outlet lines.

The liberated hydrogen chloride is preferably removed under a gentle stream of nitrogen. The resulting polyester is dried at elevated temperature, for example at about 120° C. under reduced pressure. The polyester may be purified by redissolving in one of the abovementioned solvents and precipitating in methanol.

If the polymer is soluble in the solvent which is used, the organic phase is separated off and the polyester is isolated therefrom in a conventional way, eg. by taking up in methanol and filtering off. If, on the other hand, the polymer precipitates from the solvent, or if a gel is formed, the reaction mixture is diluted if necessary, eg. with methanol, and the polymer is filtered off.

In the silyl process, the bissilylated diols are heated with the dichlorides of the dicarboxylic acids in the presence of a catalytic amount of a quaternary ammonium salt such as triethylbenzylammonium chloride without diluent or with one of the abovementioned solvents in a suitable reaction vessel described above. The resulting polyester is worked up as described above.

In the transesterification process, the free dicarboxylic acids are reacted with the acetylated diols in the presence of catalytic amounts of an alkaline metal oxide or alkaline earth metal oxide (eg. MgO) or in the presence of salts of zinc, tin, zirconium, manganese and bismuth, in a suitable reaction vessel described above without diluent. The resulting polyesters are worked up as described above.

On transesterification of a polyester (A) with free dicarboxylic acid (B) and acetylated diol (C), the reactants are employed in the A:B:C molar mass ratio of about 1–5:1–5:1–5, in particular about 1:2:2. The reaction is carried out in a suitable reaction vessel, preferably in the presence of catalytic amounts of an early transition metal alkoxide, eg. titanium tetrabutoxide. The reaction vessel is preferably flushed with nitrogen several times in order to remove air. The acetic acid liberated in the reaction is preferably removed under a gentle stream of nitrogen. The reaction is preferably continued under reduced pressure.

The resulting polyester is worked up as described above.

Polyesters which can particularly be employed are polyethylene terephthalate (PET), polybutylene terephthalate (PBT) and polyethylene naphthalate (PEN).

Of said preparation processes, the HCl process, the silyl process and the transesterification are particularly preferred.

The polyesters according to the invention have an inherent viscosity $\eta_{inh}$ of about 0.1–3 dl/g, in particular about 0.1–1.5 dl/g, measured at 20° C. with c=2 g/l in dichloromethane/trifluoroacetic acid (ratio 4/1 by volume).

The polyesters according to the invention contain randomly distributed units.

The polymers according to the invention are particularly suitable as surface-coating materials, as optical components and as chiral nematic coloring agents. They can be used as coloring surface-coating systems (eg. as automobile paint or effect sheets), or else for preparing colored pigments. The coloring structure of the polymer can moreover be fixed by rapidly cooling the chiral nematic phase. The polymers according to the invention have advantageously high glass transition temperatures (determined by DSC) of about 80–300° C., in particular about 100–220° C. At temperatures below the glass transition temperature, the coloring structure of the polymer is permanently retained without additional crosslinking. Colored pigments can be prepared, for example, by detaching the oriented polymer film from the coated surface and grinding to pigments in platelet form. In contrast to the processes described in DE-A 42 40 743, no crosslinking of the polymer is necessary in this case. The polymer can be used as surface coating system in the form of a powder, a melt or a solution (eg. in N-methylpyrrolidone or dimethylformamide). Orientation of the system takes place in the simplest case by heat treatment of the coated surface and may be improved by exposure to mechanical, electrical or magnetic forces.

The polymers according to the invention may be mixed with additional components to adjust the viscosity and the levelling behavior.

Particularly suitable as such components for paint-like coatings are polymeric binders and/or monomeric compounds which can be converted by polymerization into a polymeric binder. Examples of suitable agents of this type are polyesters, cellulose esters, polyurethanes, silicones, polyether- or polyester-modified silicones, which are soluble in organic solvents. Cellulose esters such as cellulose acetobutyrate are particularly preferably employed.

If required, stabilizers against the effects of UV and weather may be added to the surface coatings according to the invention. Suitable examples thereof are derivatives of 2,4-dihydroxybenzophenone, derivatives of 2-cyano-3,3-diphenylacrylate, derivatives of 2,2'4,4'-tetrahydroxybenzophenone, derivatives of ortho-hydroxyphenylbenzotriazole, salicylic esters, ortho-hydroxyphenyl-s-triazines or sterically hindered amines. These substances can be employed alone or, preferably, in the form of mixtures.

It is also possible to add pigments, dyes and fillers to the surface-coating systems according to the invention.

Examples of inorganic pigments are iron oxides, titanium dioxide and the various types of carbon black.

Examples of organic pigments are those from the class of monoazopigments (eg. products derived from acetoacetarylide derivatives or from β-naphthol derivatives), monoazo dyes and their metal salts such as β-hydroxynaphthoic acid dyes, disazo pigments, fused disazo pigments, isoindoline derivatives, derivatives of naphthalene- or perylenetetracarboxylic acid, anthraquinone pigments, thioindigo derivatives, azomethine derivatives, quinacridones, dioxazines, pyrazoloquinazolones, phthalocyanine pigments or basic dyes such as triarylmethane dyes and their salts.

Other suitable pigments are those giving an effect, such as aluminum particles, mica or coated mica, or the commercial effect pigments in platelet form with various chemical structures.

Examples of suitable fillers are rutile, anatase, chalk, talc and barium sulfate.

Suitable additional dyes are all those which dissolve to give a concentration of at least 0.1 mol % in the coating composition. Dichroic dyes are very particularly suitable. The total content of pigments, dyes or fillers is generally up to 40, generally 0 to 10%, of the weight of the polymers according to the invention.

The surface coating can also be carried out by a printing process.

It is possible to use for this purpose all conventional printing processes (eg. letterpress, gravure, flexographic, offset and screen printing).

Processes suitable according to the invention for coating and printing substrates are described in WO 96/02597, which is incorporated herein by reference.

The following examples illustrate the invention without, however, restricting it thereto:

The physical properties of the polymers described in the examples are indicated in Table 1.

EXAMPLE 1

Tert-butylhydroquinone (19 mmol), isosorbide (1 mmol), adipoyl chloride (2 mmol) and N-(4'-carboxyphenyl) trimellitic imide dichloride (18 mmol) and 1-chloronaphthalene (20 ml) were placed in a cylindrical glass reactor equipped with a mechanical stirrer and gas inlet and outlet. The reaction vessel was placed in an oil bath preheated to 120° C., and the temperature was rapidly raised to 230° C. The reaction mixture was stirred at 230° C. under a gentle stream of nitrogen for 8 h. After cooling, the reaction product was dissolved in dichloromethane/trifluoroacetic acid (ratio 4:1 by volume), precipitated in methanol and dried at 80° C. under reduced pressure. The resulting polyester is described by formula 1

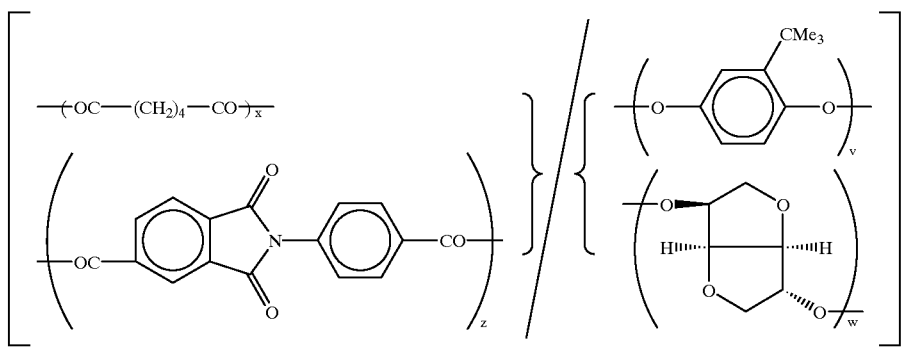

The v/w/x/z molar ratio is 19/1/2/18 (1a). Five other polyesters with v/w/x/z molar ratios of 19/1/4/16 (1b), 19/1/6/14 (1c), 19/1/8/12 (1d), 18/2/6/14 (1e) and 18/2/8/12 (1f) were prepared in a similar way. The yield was 97% for polyester 1d and 98% for each of the polyesters 1a, 1b, 1c, 1e and 1f.

EXAMPLE 2

The polyesters were prepared as in Example 1 employing phenylhydroquinone in place of tert-butylhydroquinone. Three polyesters of the formula 2 with the v/w/x/z molar ratios of 19/1/6/14 (2a), 18/2/6/14 (2b) and 18/2/8/12 (2c) were prepared. The yield was 97% for polyester 2b and 98% for each of polyesters 2a and 2c.

EXAMPLE 3

The polyesters of the formula 3

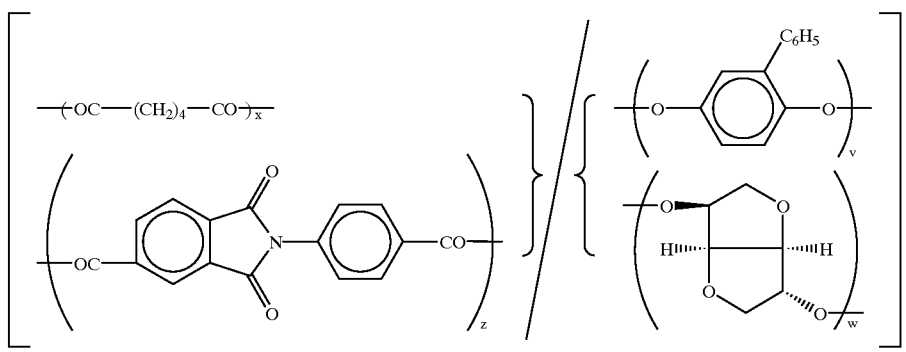

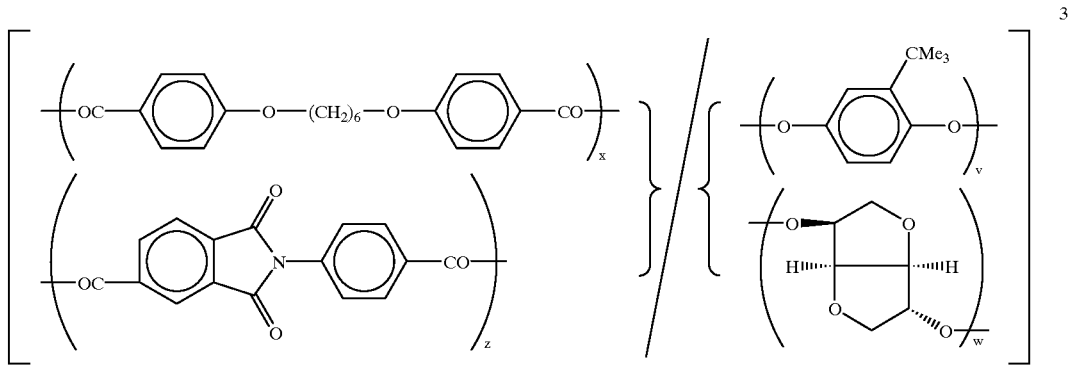

were prepared as in Example 1 replacing adipoyl chloride by the dichloride of compound I

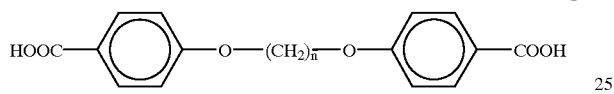

(n=6). The v/w/x/z molar ratio was 19/1/2/18 (3a), 19/1/4/16 (3b), 19/1/8/12 (3c), 18/2/4/16 (3d) and 18/2/8/12 (3e). The yield was 97% for polyesters 3c and 3e, 98% for 3b and 3d and 99% for 3a.

Another polyester of the formula 3 was prepared alternatively by the silyl process. O,O'-Bistrimethylsilyl-tert-butyl-hydroquinone (19 mmol), O,O'-bistrimethylsilylisosorbide (1 mmol), the dichloride of compound I (2 mmol) and N-(4'-carboxyphenyl)trimellitic imide dichloride (18 mmol) and triethylbenzylammonium chloride (10 mg) were placed in a cylindrical glass reactor with mechanical stirrer and gas inlet and outlet. The reaction vessel was placed in a metal bath preheated to 150° C. The temperature was increased to 260° C. and kept at this for 3 h. The pressure was reduced for 15 min. The resulting polyester was worked up as described above. The polyester contains the components of formula 3 in the v/w/x/z molar ratio of 19/1/2/18. The yield of this polymer (3fs) was 99%. Polymers 3a, 3b, 3d and 3e were likewise prepared alternatively by the silyl process. The corresponding products are referred to as 3as, 3bs, 3ds and 3es. The yields were 99% for polyesters 3as, 3bs and 3ds and 97% for 3es.

EXAMPLE 4

A polyester of the Formula 4

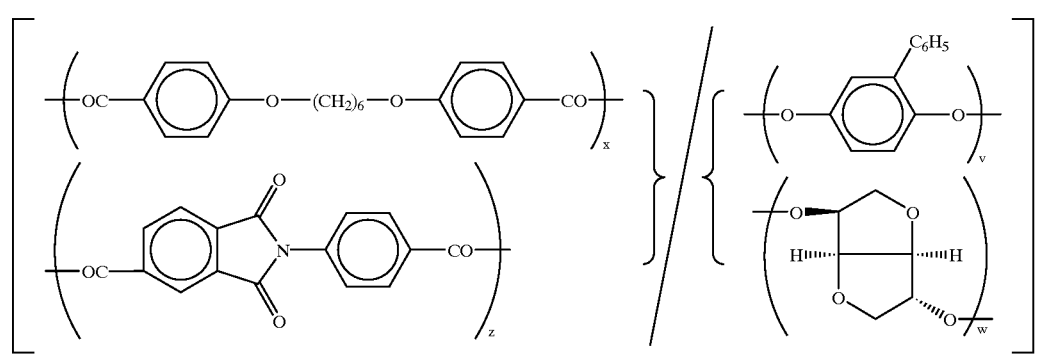

was prepared as in Example 2 replacing adipoyl chloride by the dichloride of compound I with n=6 (cf. Example 3). The v/w/x/z molar ratio was 19/1/4/16 (4a). The yield of polyester 4a was 98%.

EXAMPLE 5

A polyester of the formula 5

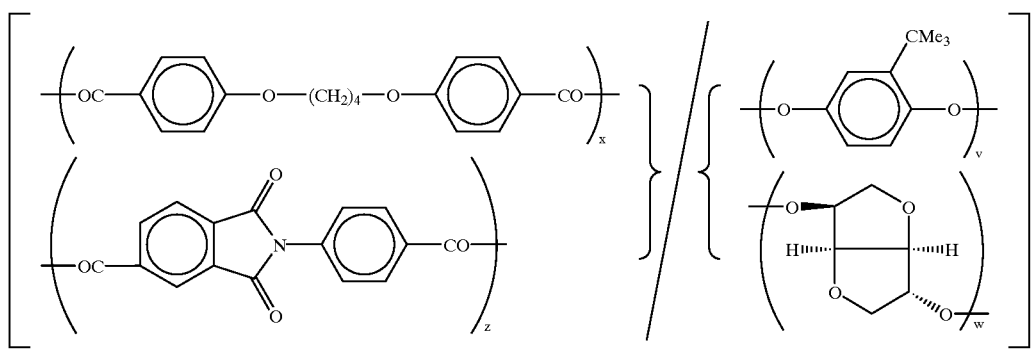

was prepared by the silyl process as in Example 3, employing the dichloride of compound I with four flexibilizing alkylene groups (n=4). The v/w/x/z molar ratio was 19/1/4/16 (5a). The yield of polyester 5a was 98%.

EXAMPLE 6

Two polyesters of the formula 6

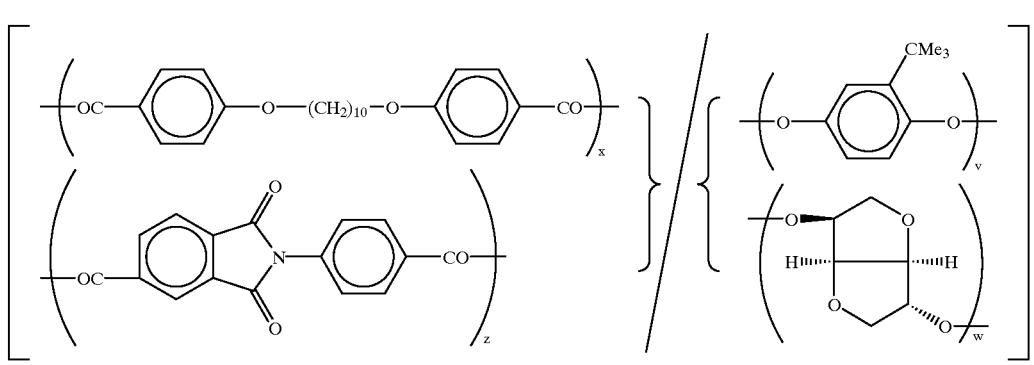

were prepared by the silyl process as in Example 3, employing the dichloride of compound I with ten flexibilizing alkylene groups (n=10). The v/w/x/z molar ratio was 19/1/4/16 (6a) or 18/2/4/16 (6b). The yield was 99% for each of 6a and 6b.

EXAMPLE 7

N-(4'-Carboxyphenyl)trimellitic imide dichloride (5 mmol), tert-butylhydroquinone (4.5 mmol), hexanediol (0.25 mmol) and isosorbide (0.25 mmol) were weighed into a glass reactor equipped with mechanical stirrer and inlet and outlet for nitrogen. After addition of 5 ml of 1-chloronaphthalene, the reactor was heated to 230° C. in a metal bath. The mixture was stirred under a gentle stream of nitrogen for 8 h at this temperature. After cooling, the crude product was dissolved in a mixture of trifluoroacetic acid and dichloromethane (ratio 1:4 by volume) and precipitated by pouring into cold methanol. The product was filtered off and then dried in a vacuum oven at 80° C. for 2 days. The u/v molar ratio in the resulting polymer of the formula 7

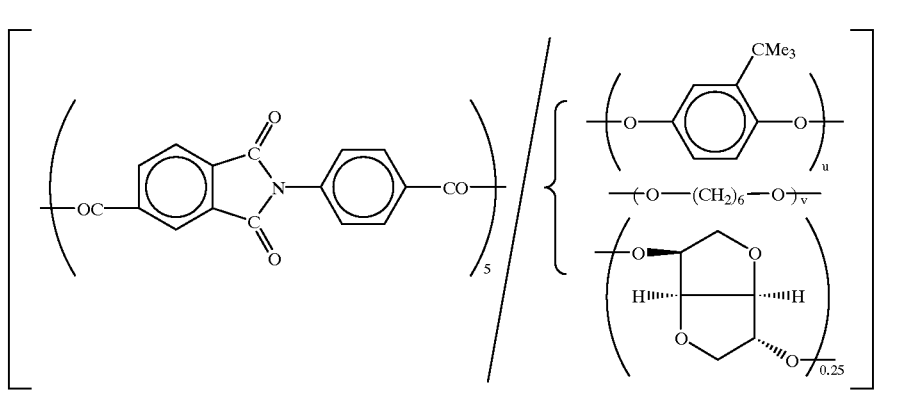

was 4.5/0.25 (7a). Two other polymers of the formula 7 were prepared in a similar way with the u/v molar ratio of 4.25/0.5 (7b) and 4/0.75 (7c). The yield was 97% for polymer 7a and 99% for each of polymers 7b and 7c.

EXAMPLE 8

The dichloride of compound I (cf. Example 3) with six flexibilizing alkylene groups (n=6) (5 mmol) and terephthaloyl chloride (5 mmol) were reacted with tert-butylhydroquinone (9.5 mmol) and isosorbide (0.5 mmol) as in Example 7. The resulting polyester of the formula 8

EXAMPLE 9

The dichloride of compound I with four flexibilizing alkylene groups (n=4) (10 mmol) was reacted with tert-butylhydroquinone (9.5 mmol) and isosorbide (0.5 mmol) as in Example 8. The resulting polyester of the formula 9

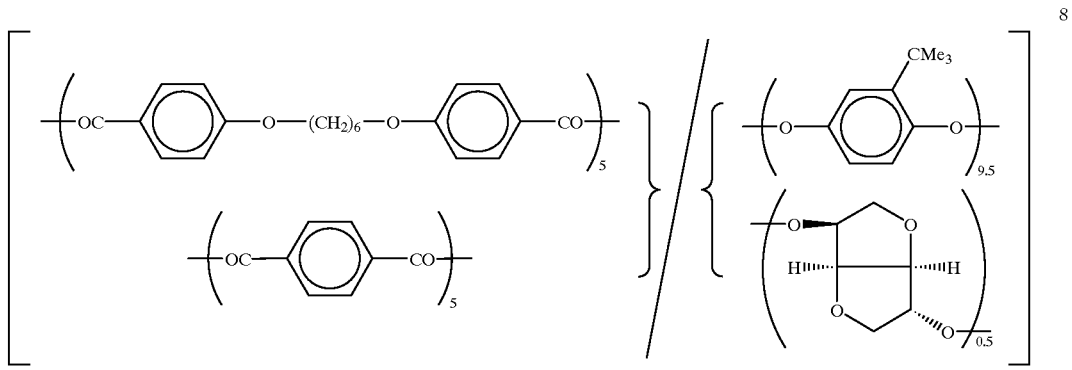

(8a) was obtained in a yield of 97%.

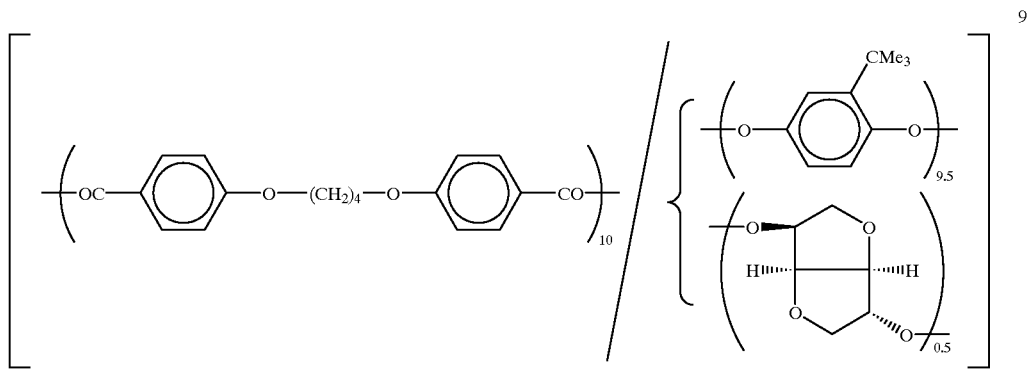

(9a) was obtained in a yield of 98%.

EXAMPLE 10

The dichloride of compound I without flexibilizing alkylene groups (n=0) (5.25 mmol), adipoyl chloride (3 mmol) and 2,6-naphthalenedicarbonyl dichloride (1.75 mmol) were reacted with tert-butylhydroquinone (9.5 mmol) and isosorbide (0.5 mmol) as in Example 9. The resulting polyester of the formula 10

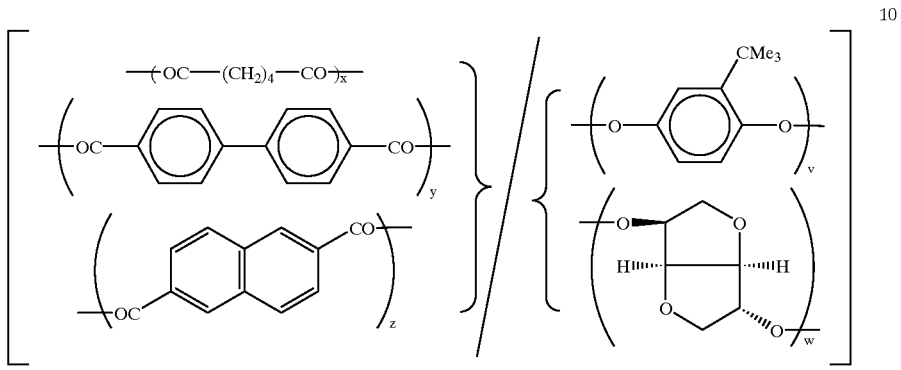

(10a) was obtained in a yield of 99%. Three other polyesters with the v/w/x/y/z molar ratio of 9.5/0.5/3/7/0 (10b), 9/1/3/7/0 (10c) and 9/1/3/5.25/1.75 (10) were prepared in a similar way. The yield of each of these three polyesters was 98%.

EXAMPLE 11

Polyethylene terephthalate (10 mmol),

N-(4'-carboxyphenyl)trimellitic imide (20 mmol), 1,4-diacetoxy-2-methylbenzene (16 mmol), diacetoxyisosorbide (4 mmol) and 20 mg of titanium tetrabutoxide were weighed into a glass reactor equipped with a mechanical stirrer and an inlet and outlet for nitrogen. The reactor had been treated with dimethyldichlorosilane and washed with dry ether before use. The reactor was placed in a metal bath preheated to 120° C. For complete removal of the air present in the reactor, it was evacuated and flushed 4 times with nitrogen. The temperature was then rapidly increased to 280° C., resulting in a homogeneous melt after 30 min, which was then stirred for 1 h. The liberated acetic acid was removed under a gentle stream of nitrogen. The pressure was reduced for 6 h while continuing the stirring. After cooling, the crude product was dissolved in a mixture of trifluoroacetic acid and dichloromethane (ratio 1:4 by volume), precipitated by pouring into cold methanol and dried at 80° C. The resulting mixed polyester was obtained in a yield of 98%.

Table 1 indicates the physical properties (inherent viscosity ($\eta_{inh}$), glass transition temperature ($T_g$) and clearing point ($T_i$), the observed textures of the liquid crystalline phases, and the interference colors of polymers 1 to 11.

TABLE 1

| Polymer | $\eta_{inh}$ [1] (dl/g) | $T_g$ [2] (° C.) | $T_i$ [3] (° C.) | Texture | Color |
|---|---|---|---|---|---|
| 1a | 0.57 | 195 | >400 | Grandjean | blue |
| 1b | 0.62 | 179 | >400 | Grandjean | blue |
| 1c | 0.41 | 147 | 350–370 | Grandjean | yellow-red |
| 1d | 0.65 | 152 | 270–280 | Grandjean | pale blue |

TABLE 1-continued

| Polymer | $\eta_{inh}$ [1] (dl/g) | $T_g$ [2] (° C.) | $T_i$ [3] (° C.) | Texture | Color |
|---|---|---|---|---|---|
| 1e | 0.40 | 138 | 330–350 | Grandjean | blue-green |
| 1f | 0.61 | 142 | 240–260 | Grandjean | green |
| 2a | 0.44 | 121 | 320–340 | Grandjean | yellow-orange |
| 2b | 0.21 | 100 | 260–270 | Grandjean | blue-green |
| 2c | 0.21 | 87 | 200–205 | Grandjean | pale blue |
| 3a | 0.48 | 195 | >400 | Grandjean | blue |
| 3b | 0.64 | 177 | >400 | Grandjean | blue |
| 3c | 0.54 | 126 | >400 | Grandjean | blue |
| 3d | 0.73 | 175 | >400 | Grandjean | blue |
| 3e | 0.27 | 129 | >400 | Grandjean | blue |
| 3as | 0.83 | 194 | >400 | Grandjean | blue-green |
| 3bs | 0.64 | 177 | >400 | Grandjean | green, orange |
| 3ds | 0.78 | 174 | >400 | Grandjean | blue |
| 3es | 1.14 | 164 | >400 | Grandjean | blue |
| 3fs | 0.60 | 193 | >400 | Grandjean | blue-green |
| 4a | 0.55 | 135 | 360–375 | Grandjean | blue |
| 5a | 0.55 | 178 | >400 | Grandjean | beige/red |
| 6a | 0.38 | 160 | 380–400 | Grandjean | yellow |
| 6b | 0.44 | 159 | >400 | Grandjean | blue |
| 7a | 0.26 | 170 | 380–400 | Grandjean | yellow-green |
| 7b | 0.28 | 153 | 380–390 | Grandjean | green |
| 7c | 0.34 | 150 | 360–380 | Grandjean | blue |
| 8a | 0.25 | 80 | 190–200 | Grandjean | blue |
| 9a | 0.28 | 108 | 230–240 | Grandjean | blue |
| 10a | 0.35 | 125 | >400 | Grandjean | red-orange |
| 10b | 0.40 | 148 | >400 | Grandjean | blue |
| 10c | 0.35 | 139 | >400 | Grandjean | blue |
| 10d | 0.41 | 128 | >400 | Grandjean | blue |
| 11 | 0.53 | 119 | >400 | Grandjean | green |

[1] Measured at 20° C., c = 2 g/l in dichloromethane/trifluroacetic acid (4/1)
[2] DSC measurement, heating rate 20° C./min
[3] Optical microscope heating rate 10° C./min
411/hz/bw

We claim:

1. A chiral nematic polyester with flexible chains which comprise isosorbide, isomannide and/or isoidide units and, for flexibilization of the chains, contain at least one unit derived from a member selected from the group consisting of (a) aliphatic dicarboxylic acids,
   (b) aromatic dicarboxylic acids with a flexible spacer,
   (c) α,ω-alkanediols, and
   (d) condensates of a polyalkylene terephthalate or polyalkylene naphthalate with an acylated diphenol and an acylated isosorbide.

2. A chiral nematic polyester as claimed in claim 1, wherein units (a) are represented by the formula

wherein n is a number in the range from 3 to 15;
   units (b) are represented by the formula

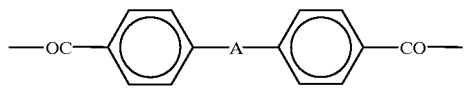

wherein
   A is $(CH_2)_n$, $O(CH_2)_nO$ or $(CH_2)_o$—O—$(CH_2)_p$,
   n is a number in the range from 3 to 15, and
   o and p are, independently of one another, a number in the range from 1 to 7;
   units (c) are represented by the formula

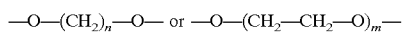

wherein
   n is a number in the range from 3 to 15, and
   m is a number in the range from 1 to 10.

3. A chiral nematic polyester as claimed in claim 1, which contains as nonflexible acid component units of the formula

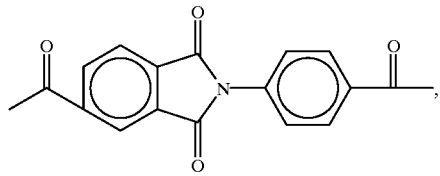

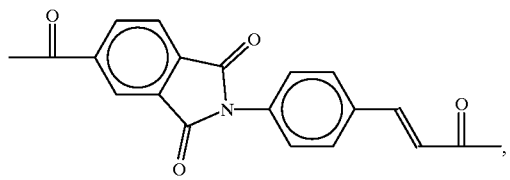

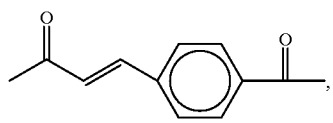

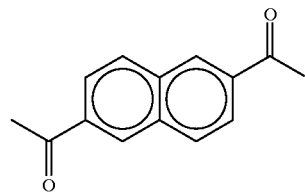

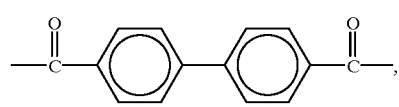

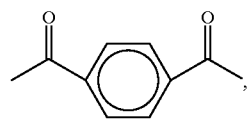

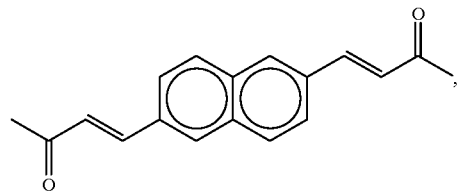

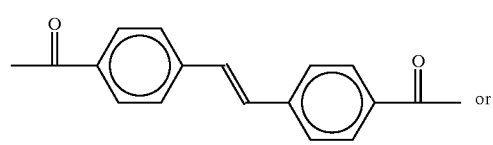

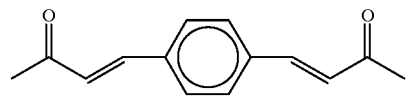

or and as nonflexible alcohol component diol units of the formula

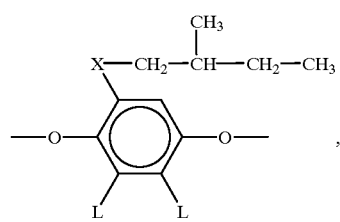

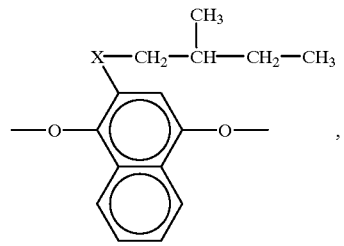

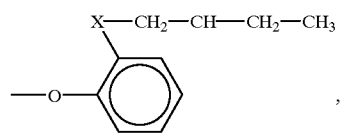

-continued

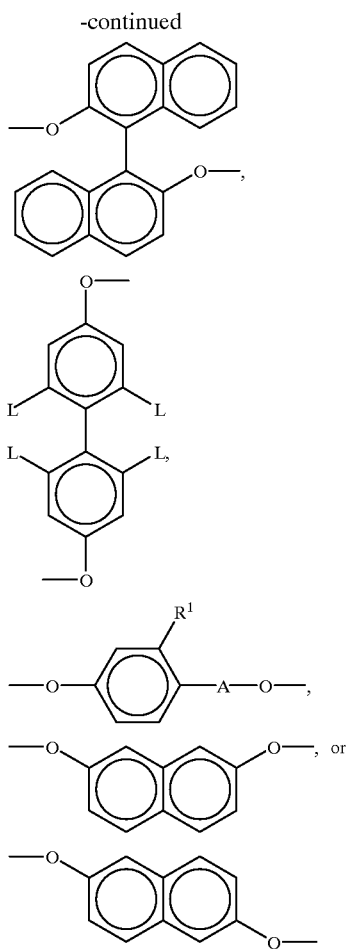

wherein

L is alkyl, alkoxy, halogen, COOR, OCOR, CONHR or NHCOR,

X is S, O, N, CH$_2$ or a single bond,

A is a single bond,

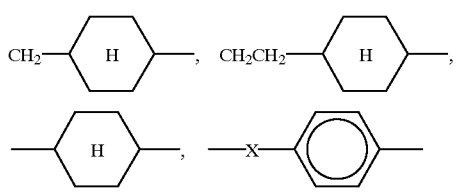

or

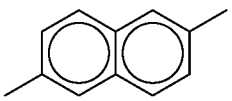

and

R$^1$ is hydrogen, halogen, alkyl or phenyl, and

R is alkyl or hydrogen.

4. A chiral nematic polyester as claimed in claim 1, which contains from 1 to 15 mol % of isosorbide, -mannide and/or -idide units.

5. A chiral nematic polyester as claimed in claim 1, which contains from 1 to 50 mol % of units of flexibilizing the polyester chain.

6. A chiral nematic polyester as claimed in claim 1, having an inherent viscosity of about 0.10 to 3 dl/g when measured at 20° C.

7. A chiral nematic polyester as claimed in claim 1, having glass transition temperature from about 80 to 300° C.

8. A chiral nematic polyester as claimed in claim 1, wherein (a) is adipic acid.

9. An optical component comprising a chiral nematic polyester as claimed in claim 1.

10. A surface coating material comprising a chiral nematic polyester as claimed in claim 1.

11. A coloring agent comprising a chiral nematic polyester as claimed in claim 1.

12. The coloring agent of claim 11, selected from the group consisting of coloring components of surface-coating systems and components of printing inks.

13. A cosmetic composition comprising a chiral nematic polyester as claimed in claim 1.

14. The cosmetic composition of claim 13, selected from the group consisting of nail varnishes and lipsticks.

15. A pigment comprising a chiral nematic polyester as claimed in claim 1.

16. A coating composition comprising at least one chiral nematic polyester as claimed in claim 1.

17. A coating composition comprising at least one pigment as claimed in claim 15.

18. A process for preparing chiral nematic polyesters as claimed in claim 1, which comprises reacting free diols with dicarbonyl dichlorides in an inert aromatic solvent.

19. The process of claim 18, wherein the inert aromatic solvent is 1-chloronaphthalene.

20. A process for preparing chiral nematic polyesters as claimed in claim 1, which comprises reacting silylated diols with dicarbonyl dichlorides without diluent.

21. A process for preparing chiral nematic polyesters as claimed in claim 1, which comprises reacting acetylated diols with free dicarboxylic acids.

22. A process for preparing chiral nematic polyesters as claimed in claim 1, which comprises reacting a mixture of free dicarboxylic acids and acetylated diols with a polyester.

23. The process of claim 22, wherein the polyester is polyethylene terephthalate, polybutylene terephthalate or polyethylene naphthalate.

* * * * *